United States Patent [19]
Takahashi et al.

[11] Patent Number: 4,844,788
[45] Date of Patent: Jul. 4, 1989

[54] WIDE-RANGE AIR/FUEL RATIO SENSOR AND DETECTOR USING THE SAME

[75] Inventors: Hideaki Takahashi, Aichi; Haruyoshi Kondo, Anjo; Keiichi Saji, Aichi, all of Japan

[73] Assignee: Kabushiki Kaisha Toyota Chuo Kenkyusho, Aichi, Japan

[21] Appl. No.: 263,875

[22] Filed: Oct. 28, 1988

[30] Foreign Application Priority Data

Nov. 4, 1987 [JP] Japan ............................ 62-277308

[51] Int. Cl.$^4$ ............................................ G01N 27/58
[52] U.S. Cl. .................................. 204/406; 204/412; 338/34
[58] Field of Search ............... 204/412, 406, 425, 426; 338/34; 60/276; 123/489

[56] References Cited

U.S. PATENT DOCUMENTS 4,500,412  2/1985  Takahashi et al. .................. 204/425
4,595,485  6/1986  Takahashi et al. .................. 204/406
4,661,234  4/1987  Takahashi et al. .................. 204/406

Primary Examiner—G. L. Kaplan
Attorney, Agent, or Firm—Oblon, Spivak, McClelland, Maier & Neustadt

[57] ABSTRACT

An air/fuel ratio sensor has a porous alumina substrate, a limiting current type oxygen detecting section on the porous alumina substrate for detecting the air/fuel ratio in the fuel lean region, a resistance-variable type oxygen detecting section on the porous alumina substrate for detecting the excess air ratio λ when λ is equal to one, a gas decomposition type hydrogen detecting section on the porous alumina substrate for detecting the air/fuel ratio in the fuel rich region and a heater for heating the respective detecting sections to the optimum temperature in operation, whereby the sensor can detect the air/fuel ratio over all the fuel rich and lean regions.

In addition the apparatus includes a comparing/discriminating section for comparing the output of the resistance-variable type oxygen detecting section with a reference value to discriminate whether the ambient atmosphere is in either of the fuel rich or lean region, a switching control section for changing each of the limiting current type oxygen detecting section from its operative position to its inoperative position or vice versa, depending on the result from the comparing/discriminating section, and an output signal adding section for adding the output signals from both the detecting sections to generate an output signal representative of an air/fuel ratio.

14 Claims, 13 Drawing Sheets

WIDE-RANGE AIR/FUEL RATIO SENSOR AND DETECTOR USING THE SAME

BACKGROUND OF THE INVENTION

1. Field of the Invention

The present invention relates to a wide-range air/fuel ratio sensor for performing the accurate detection of the air/fuel ratio over a wide measurement range and also to a detector using the same.

2. Description of the Related Art

Sensors capable of continuously measuring the air/fuel ratio of the exhaust gas from vehicles such as motor cars and the like over a wide measurement range and which can be mass-produced with their reduced dimensions have been developed recently from the sintered green sheet technique and film printing technique. Such sensors includes a limiting current type oxygen sensor having an atmosphere reference (disclosed in Japanese Patent Application No. 56-123373), a wide-range air/fuel ratio sensor comprising, in combination, an oxygen concentration cell type element and an oxygen pump element (disclosed in Japanese Patent Application No. 58-237626 and "Sensor and Actuators", 2 (1982), pages 371–384) and so on. There is also known an integral sensor unit comprising a combination of a limiting current type oxygen sensor having an alumina substrate not exposed to the ambient air with a resistance-variable type $\lambda = 1$ sensor, the integral sensor unit adapted to measure the air/fuel ratio in the range from $\lambda = 1$ to the fuel lean region (U.S. Pat. No. 4,661,234). All these sensors are adapted first to measure the amount of oxygen in the exhaust gas and then to detect the air/fuel ratio therein from the measured results of the oxygen.

SUMMARY OF THE INVENTION

From investigation of the composition of combustion gas exhausted from vehicles, it has been found that the concentration of combustible gas including CO, $H_2$ and others decreases as the excess air ratio approaches one and that the concentration of combustible gas becomes substantially equal to zero in the fuel lean region wherein the excess air ratio $\lambda$ is higher than one. On the contrary, the concentration of $O_2$ gas becomes equal to zero in the fuel rich region and increases on the variation of the excess air ratio from one to the fuel lean region. It is therefore preferred that the concentration of $O_2$ gas is monitored to measure the air/fuel ratio in the fuel lean region and that the concentration of CO, $H_2$ and other gases is monitored to measure the air/fuel ratio in the fuel rich region. It has been found that the air/fuel ratio can be estimated from these measured concentrations more accurately than that from the prior art systems which are adapted to determine the air/fuel ratio only from the concentration of oxygen gas.

It is therefore an object of the present invention to provide an air/fuel ratio sensor and an apparatus using the same which can continuously measure the air/fuel ratio over an increased measurement range from the fuel rich region to the fuel lean region with an increased accuracy.

To this end, the present invention provides an air/fuel ratio sensing system comprising a single porous alumina substrate, a resistance-variable type oxygen detecting section (oxide semiconductor detecting section), a limiting current type oxygen detecting section and a gas decomposition type hydrogen detecting sections, which sections are arranged in combination on the porous alumina substrate and can be selected with respect to their good ranges, respectively.

In one aspect of the present invention, it provides a wide range air/fuel ratio sensor comprising a porous alumina substrate; a limiting current type oxygen detecting section for detecting the air/fuel ratio in the fuel lean region, said oxygen detecting section being in the form of a lamination consisting of a first gas-permeable electrode layer on the porous alumina substrate, a solid electrolytic layer on the first layer and a second gas-permeable electrode layer on the solid electrolytic layer; a resistance-variable type oxygen detecting section for detecting the excess air ratio when being equal to one (1), said resistance-variable type oxygen detecting section consisting of an oxide semiconductor layer and a pair of opposite electrodes all of which are disposed on the porous alumina substrate; a gas decomposition type hydrogen detecting section for detecting the air/fuel ratio in the fuel rich region, said hydrogen detecting section being in the form of a lamination consisting of a second gas-permeable electrode layer on said porous alumina substrate, a solid electrolytic layer on the second electrode layer and a first gas-permeable electrode layer on the solid electrolytic layer;-and a heater for heating the respective detecting sections.

In the second aspect of the present invention, it provides a wide range air/fuel ratio detecting apparatus comprising the aforementioned wide-range air/fuel ratio sensor; a comparator/discriminator for comparing the output of the resistance-variable type oxygen detecting section in said wide-range air/fuel ratio sensor with a reference value and for discriminating whether said output is in the fuel rich or lean region; a switching control section in response to the output of said comparator/discriminator for changing said limiting current type oxygen detecting section to its operative position and said gas decomposition type hydrogen detecting section to its inoperative position when said comparator/discriminator discriminates the change from the fuel rich region to the fuel lean region and for changing said limiting current type oxygen detecting section to its inoperative position and said gas decomposition type hydrogen detecting section to its operative position when said comparator/discriminator discriminates the change from the fuel lean region to the fuel rich region; and an output signal adding section for adding an output signal from said limiting current type oxygen detecting section and an output signal from said gas decomposition type hydrogen detecting section to each other and generating an output signal representative of an air/fuel ratio from the added output signals.

As is apparent from the foregoing, the wide-range air/fuel ratio sensor constructed in accordance with the first aspect of the present invention comprises a common porous alumina substrate, a resistance-variable type oxygen detecting section having its resistance which is abruptly changed at a point wherein the excess air ratio is equal to one, a limiting current type oxygen detecting section having its output current linearly increasing in response to the concentration of oxygen in the fuel lean region, and a gas decomposition type hydrogen detecting section having its output current increasing in response to the concentration of hydrogen in the fuel rich region, all of which sections are formed on the common porous alumina substrate. Therefore, the sensor will be operated to sense the air/fuel ratio in the fuel lean region by the use of the limiting current type oxygen detecting section and to detect the air/fuel ratio in the fuel rich region by the use of the gas decomposition type hydrogen detecting section, such that the detecting sections will be switched from one section to another to be used compatible with the region used. Thus, the wide range air/fuel ratio sensor of the present invention can detect the air/fuel ratio over an increased measurement range more accurately than the prior art systems in which a single type of sensor is only utilized. Furthermore, all the detecting sections are integrally formed on a single porous alumina substrate together with the resistance-variable type oxygen detecting section used to discriminate the region presently used therein. Since all the components are thus arranged in close proximity with one another on the porous alumina substrate, the state (region) under which the detecting sections other than the resistance-variable type oxygen detecting section are located can more accurately be discriminated by the resistance-variable type oxygen detecting section. This means that the measurement of air/fuel ratio at each of the detecting sections can be stably performed at a proper timing to further improve the accuracy of measurement. In addition, this provides an advantage in that the entire sensor can be reduced in size.

The wide-range air/fuel ratio detecting apparatus constructed in accordance with the second aspect of the present invention comprises, in combination, the wide-range air/fuel ratio sensor constructed in accordance with the first aspect of the present invention and circuit means for processing the output of the air/fuel ratio sensor.

The comparator/discriminator of the air/fuel ratio detecting apparatus compares the output of a resistance detector for detecting the resistance in the resistance-variable type oxygen detecting section with a reference value with the result thereof being used to discriminate whether the output of the resistance detector is in the fuel rich or lean region.

The output signal adding section adds output signals from the limiting current type oxygen detecting section, resistance-variable type oxygen detecting section and gas decomposition type hydrogen detecting section so as to generate a signal representing an air/fuel ratio from the added output signals.

The switching controller is in response to the output of the comparator/discriminator to place the gas decomposition type hydrogen detecting section in its inoperative position and the limiting current type oxygen detecting section in its operative position, after a period of time from when the comparator/discriminator discriminates the change from the fuel rich region to the fuel lean region. When the comparator/discriminator discriminates the change from the fuel lean region to the fuel rich region, the switching controller then changes the limiting current type oxygen detecting section to its inoperative position and the gas decomposition type hydrogen detecting section to its operative position. Concretely, such switching control can be attained by controlling the connection and disconnection of a source of measuring voltage with the respective detecting sections.

In such a manner, the air/fuel ratio can be measured more accurately over an increased measurement range by the fact that the resistance-variable type oxygen detecting section discriminates either of the fuel rich or lean region and that the the controller controls the connection with the respective detecting sections (limiting current type oxygen detecting section and gas decomposition type hydrogen detecting section) and that the output signals from the respective detecting sections are added to generate a signal representative of an air/fuel ratio.

In one embodiment of the wide-range air/fuel ratio detecting apparatus according to the present invention, the comparator/discriminator has its reference value set at a higher level such that the discrimination can be performed more rapidly on the change from the fuel lean region to the fuel rich region. This can eliminate a spike noise which is otherwise produced on the change from the fuel lean region to the fuel rich region.

In another embodiment of the wide-range air/fuel ratio detecting apparatus according to the present invention, the output signal adding section includes an inversion adder having its input connected with a level regulator. Thus, the output signal adding section uses the output signal from the comparator/discriminator and a direct current bias signal to generate a bias signal in the fuel lean region, different from that in the fuel rich region. The inversion adder adds the bias signal with the output signals from the limiting current type oxygen detecting section and gas decomposition type hydrogen detecting section. Thus, a one-dimensional detection output can be obtained.

DETAILED DESCRIPTION OF THE PREFERRED EMBODIMENTS

The present invention will now be described in detail with reference to some embodiments thereof.

(I) Air/Fuel Ratio Sensor

Figure 1:
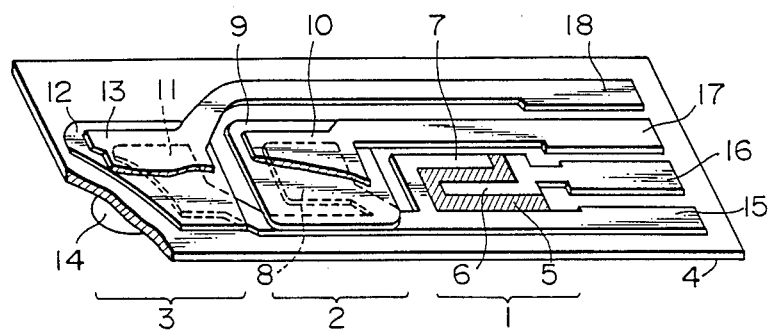
FIG. 1 is a perspective view of the outline of an air/fuel ratio sensor constructed in accordance with the present invention.
Figure 2:
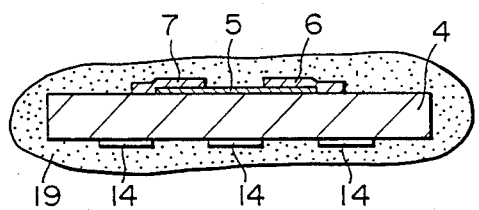
FIG. 2 is a cross-sectional view of the resistance-variable type oxygen detecting section shown in FIG. 1.
Figure 3:
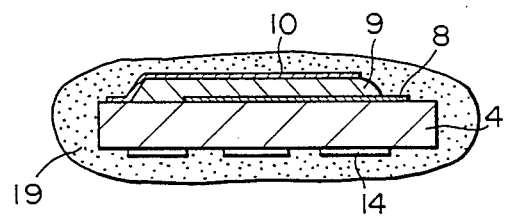
FIG. 3 is a cross-sectional view of the limiting current type oxygen detecting section shown in FIG. 1.
Figure 4:
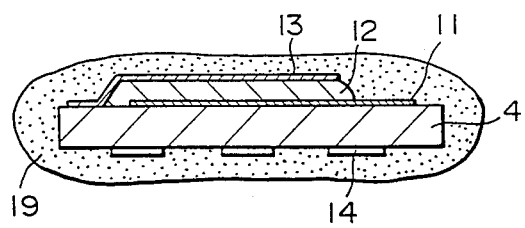
FIG. 4 is a cross-sectional view of the gas decomposition type hydrogen detecting section shown in FIG. 1.

FIG. 1 is a perspective view showing the basic arrangement of a wide-range air/fuel ratio sensor constructed in accordance with one embodiment of the present invention; FIG. 2 is a cross-sectional view of a resistance-variable type oxygen detecting section 1; FIG. 3 is a cross-sectional view of a limiting current type oxygen detecting section 2; and FIG. 4 is a cross-sectional view of a gas decomposition type hydrogen detecting section 3.

The air/fuel sensor of the present invention comprises the resistance-variable type oxygen detecting section 1 for detecting the excess air ratio when it is equal to one; the limiting current type oxygen detecting section 2 for detecting the air/fuel ratio in the fuel lean region; and the gas decomposition type hydrogen detecting sections 3 for detecting the air/fuel ratio in the fuel rich region, all the detecting sections being integrally arranged in parallel on a single porous alumina substrate 4.

The porous alumina substrate 4 has a porosity ranged from 2% to 40% and a pore diameter ranged from 0.02 μm to 1.2 μm. The substrate includes one side on which a heater is provided to heat the respective detecting sections 1, 2 and 3. Further, the entire sensor is coated with a porous layer 19 which carries a catalyst.

Each of the respective detecting sections will sequentially be described below:

(a) Resistance-Variable Type Oxygen Detecting Section

As shown in FIGS. 1 and 2, the resistance-variable type oxygen detecting section 1 comprises an oxide semiconductor layer 5 made of niobium pentaoxide ($Nb_2O_5$) as a material sensing the excess air ratio λ equal to one and formed on the aforementioned porous alumina ($Al_2O_3$) substrate 4, and electrodes 6 and 7 formed on the oxide semiconductor layer 5, opposed to each other. These electrodes 6 and 7 are connected with terminals 15 and 16, respectively.

The other face of the porous alumina substrate 4 includes heaters 14 formed thereon and made of platinum.

A porous coating layer 19 carrying a catalyst is formed around the overall surface of the sensor to prevent the deposition of unburned components onto the respective detecting sections and also to create the complete burning reaction between any unburned component going to the sensors and the oxygen. The thickness and mean pore opening of the porous coating layer 19 is so selected that the ratio of thickness to mean pore opening will be ranged from 50 to 3000. The catalyst carried on the porous coating layer 19 is preferably selected from a group consisting of palladium (Pd), rhodium (Rh), platinum (Pt) and a mixture thereof. The amount of catalyst carried on the coating layer 19 is suitably ranged from 0.001% to 50% by weight.

Figure 5:
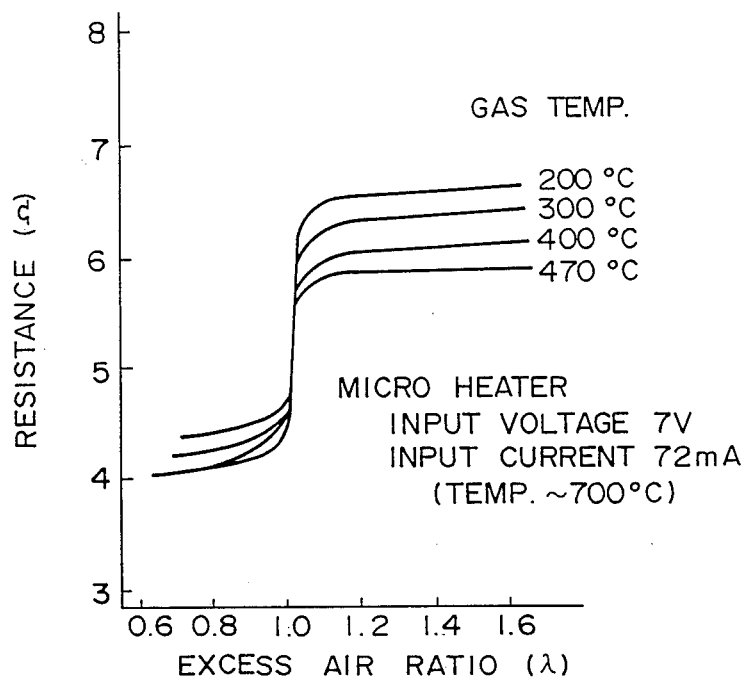
FIG. 5 is a graph showing the relationship between the resistance R of a $\lambda = 1$ sensor and the excess air ratio $\lambda$.

The resistance-variable type oxygen detecting section 1 has its resistance abruptly varying at the excess air ratio λ=1 without influence from the variations of gas temperature, as seen from the resistance-excess air ratio characteristics shown in FIG. 5.

Although in the present embodiment, the sensor 1 is made of $Nb_2O_5$, the other oxide semiconductors such as $TiO_2$, $CeO_2$ and $SnO_2$ may be used. In any event, the film thickness of the sensor is preferably ranged from 0.1 μm to 30 μm.

If the porous alumina substrate 4 also contains a catalyst, the resistance-variable type oxygen sensor 1 will be subjected to oxidation-reduction reaction from both the catalysts on the substrate 4 and coating layer 19 to provide a high-speed response.

(b) Limiting Current Type Oxygen Detecting Section

As shown in FIGS. 1 and 3, the film-like limiting current type oxygen detecting section 2 is of a laminated construction which consists of a first gas-permeable electrode (cathode) 8 made of platinum and deposited on the porous alumina substrate 4; a solid electrolytic layer 9 disposed on the first electrode 8, the solid electrolytic layer 9 being made of $ZrO_2+Y_2O_3$ which has a crystalline orientation in a particular direction and a film thickness ranged from 0.1 μm to 30 μm; and a second gas-permeable electrode (anode) 10 made of platinum and deposited on the solid electrolytic layer 9.

The opposite surface of the porous alumina substrate 4 is provided with heaters 14 of platinum for heating the limiting current type oxygen detecting section 2 to the optimum temperature in operation.

At the limiting current type oxygen detecting section 2, the porous alumina substrate 4 determines the rate of oxygen supplied thereto.

The oxygen gas subjected to the rate-determination by the porous alumina substrate 4 is then converted into oxygen ions at the boundary between the solid electrolytic layer 9 and the cathode 8. These oxygen ions travels through the solid electrolytic layer 9 toward the anode 10. At the boundary between the solid electrolytic layer 9 and the anode 10, the oxygen ions are converted again into gaseous oxygen which in turn is discharged to the exterior.

Figure 6A:
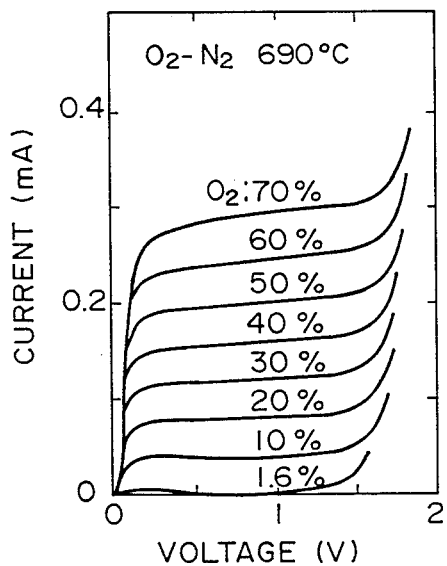
FIG. 6A is a graph showing the current-voltage characteristics in the limiting current type oxygen detection.
Figure 6B:
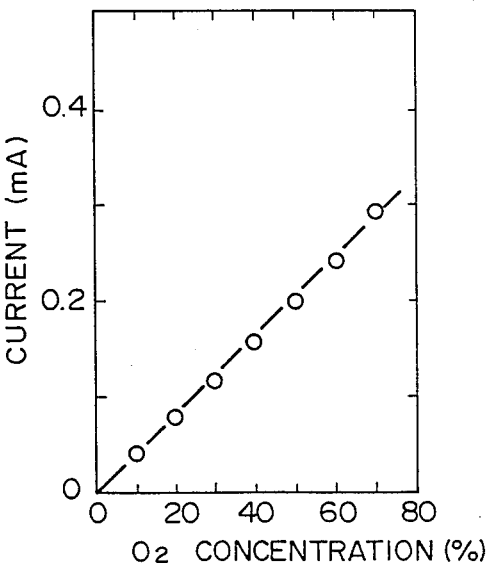
FIG. 6B is a graph showing the current-oxygen concentration characteristics in the limiting current type oxygen detection.

The limiting current type oxygen detecting section 2 had such voltage-current characteristics as shown in FIG. 6A and such a relationship between the concentration of oxygen and the output current as shown in FIG. 6B.

(c) Gas Decomposition Type Hydrogen Detecting Section

The gas decomposition type hydrogen detecting section 3 is of substantially the same construction as that of the limiting current type oxygen detecting section 2. As shown in FIGS. 1 and 4, the gas decomposition type hydrogen detecting section 3 is in the form of a lamination which consists of a second gas-permeable electrode (anode) 11 made of platinum and deposited on the porous alumina substrate 4; a solid electrolytic layer 12 disposed on the second electrode 11, the solid electrolytic layer 12 being made of $ZrO_2+Y_2O_3$ which has a crystalline orientation in a particular direction and a film thickness ranged from 0.1 $\mu$m to 30 $\mu$m; and a first gas-permeable electrode (cathode) 13 made of platinum and deposited on the solid electrolytic layer 9.

The opposite surface of the porous alumina substrate 4 is provided with heaters 14 of platinum for heating the gas decomposition type hydrogen detecting section 3 to the optimum temperature in operation.

In the prior art, the limiting current type oxygen sensor comprises electrodes disposed on the opposite faces of an electrolytic zirconia layer. One of the electrodes determining the rate of oxygen gas is utilized as a cathode while the other electrode is used as an anode. When a constant voltage is applied between these electrodes, the sensor generates an output which is used to measure the concentration of oxygen. If the ambient atmosphere becomes the fuel rich state in such an arrangement, however, an electric current not relating to the concentration of oxygen will flow between the electrodes. It becomes impossible to measure the output current proportional to the concentration of oxygen. Thus, the inventors has thought that if a gas decomposition type hydrogen sensor for measuring the concentration of hydrogen which is constructed in accordance with the following concept is used, the concentration of hydrogen ($H_2$ concentration) can be measured even in the fuel rich state.

In the concept of the present invention, the gas decomposition type hydrogen sensor is made of the same materials and constructed in the same manner as in the limiting current type oxygen sensor. However, the gas decomposition type hydrogen sensor is adapted to receive a voltage having its polarity different from that of the limiting current type oxygen sensor. One of the electrodes 11 determining the rate of oxygen gas is utilized as an anode while the opposite electrode 13 is used as a cathode. Thus, oxygen can be drawn from the cathode 13 to the anode 11 under the oxygen pump action. On the other hand, combustible gas ($H_2$) diffuses toward the anode in the porous alumina substrate 4 under the gas diffusion and rate-determination since the substrate is in the fuel rich state. The combustible gas ($H_2$) reacts with oxygen drawn from the cathode 13 to the anode 11 to reduce the partial pressure of oxygen. There will be created a difference in the concentration of oxygen between the anode 11 and the cathode 13, with the anode 11 having a reduced concentration of oxygen. As a result, an electromotive force equal to about minus one volt is produced between the anode 11 and the cathode 13. As the minus applied voltage increases, the gas components, such as $H_2O$, $CO_2$, CO and others, in the exhaust gas reaching the cathode are correspondingly subjected to the following electrochemical decomposition reaction adjacent the boundary between the Pt electrode and the $ZrO_2$ electrolytic layer under the catalytic action of platinum:

$CO_2 \rightarrow CO + \frac{1}{2}O_2$;

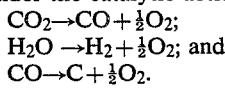

$CO \rightarrow C + \frac{1}{2}O_2$.

Oxygen gas so produced is converted into oxygen ions at the cathode 13, which oxygen ions then travels through the solid electrolytic layer 12 to the anode 11 at which the oxygen ions are returned into oxygen gas. In such a case, however, the exhaust gas contains more combustible gas components, that is, $H_2$, CO, HC and others since the present state is in the fuel rich region. Therefore, these combustible gas components are subjected to the following reaction at or adjacent the anode 11 to consume the oxygen gas:

$CO + O_2 \rightarrow 2CO_2$; and

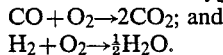

In such a manner, the concentration of the oxygen gas produced at the anode 11 can always be balanced with the voltage applied to the opposite electrodes and maintained at a level lower than that of the cathode 13.

In other words, the system acts to maintain the amount of oxygen produced at the anode 11 such that the amount of combustible gas diffusing to the anode 11 through the porous alumina substrate 4 will be balanced with the oxygen in stoichiometric ratio.

In this connection, the combustible gas contains various gas components such as $H_2$, CO, HC and others. When the combustible gas diffuses through the porous alumina substrate 4, the characteristics of the sensor varies depending on the differential diffusion between the respective gas components. Hydrogen among such gas components has its diffusion rate higher than those of the other gas components.

In case where the fuel is very rich, the rate of hydrocarbon which is hardly combustible increases while the amount of hydrogen which is easily combustible decreases up to a relatively low level. This tends to create a partial combustion. If the cathode 13 is exposed to the partial combustion state, the decomposition reaction of HC produces adjacent the cathode such that carbon will be separated out adjacent the boundary between the cathode 13 and the solid electrolytic layer 12 of $ZrO_2$. This may increase the resistance at that boundary to abruptly degrade the sensitivity of the sensor.

In accordance with the present invention, therefore, the cathode 13 in the gas decomposition type hydrogen detecting section is protected by the porous coating layer 19 to prevent the cathode 13 from being contacted directly by the exhaust gas in the partial combustion. And yet, the porous coating layer 19 contains a catalyst such as Pt, Pd or Rh in a single or mixture form. Therefore, the gas components such as CO, HC and others reaching the surface of the sensor is subjected to the decomposition reaction under the action of the catalyst on the porous coating layer 19. The carbon component produced by the decomposition reaction cannot reach the surface of the cathode 13.

Figure 7A:
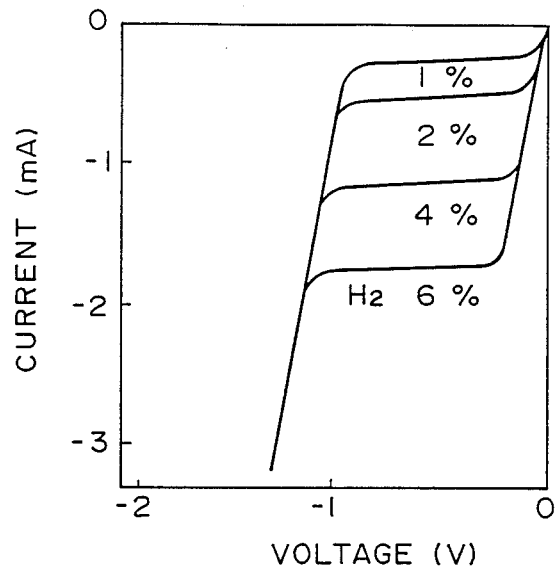
FIG. 7A is a graph showing the current-voltage characteristics in the gas decomposition type hydrogen sensor.
Figure 7B:
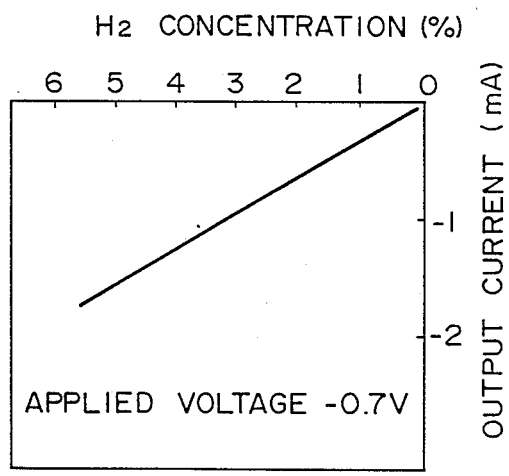
FIG. 7B is a graph showing the current-hydrogen concentration characteristics in the gas decomposition type hydrogen sensor.
Figure 8A:
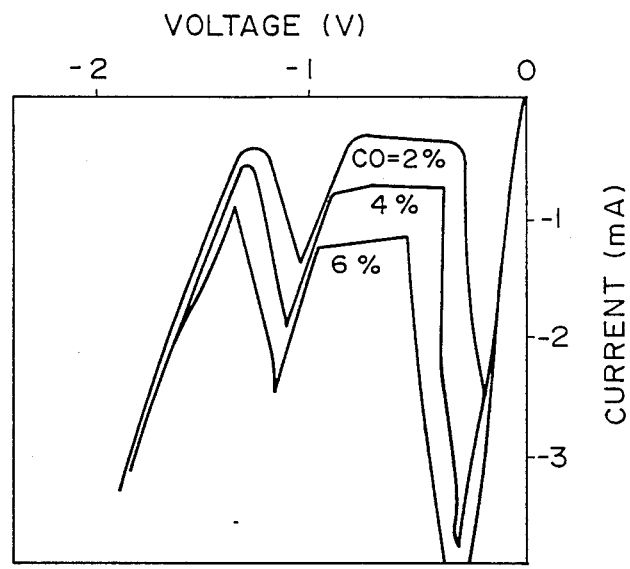
FIG. 8A is a graph showing the current-voltage characteristics in the gas decomposition type hydrogen sensor.
Figure 8B:
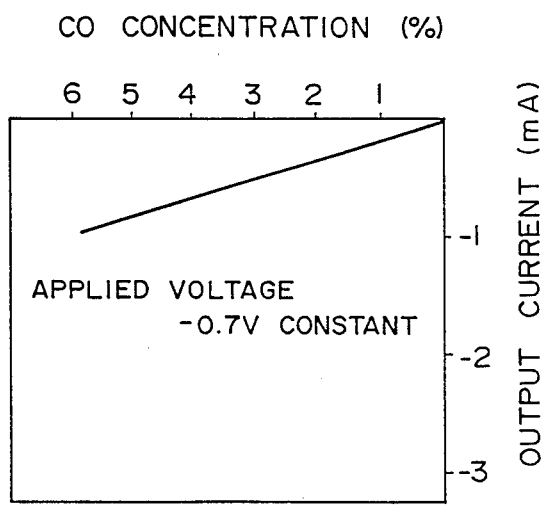
FIG. 8B is a graph showing the current-CO concentration characteristics in the gas decomposition type hydrogen sensor.
Figure 9A:
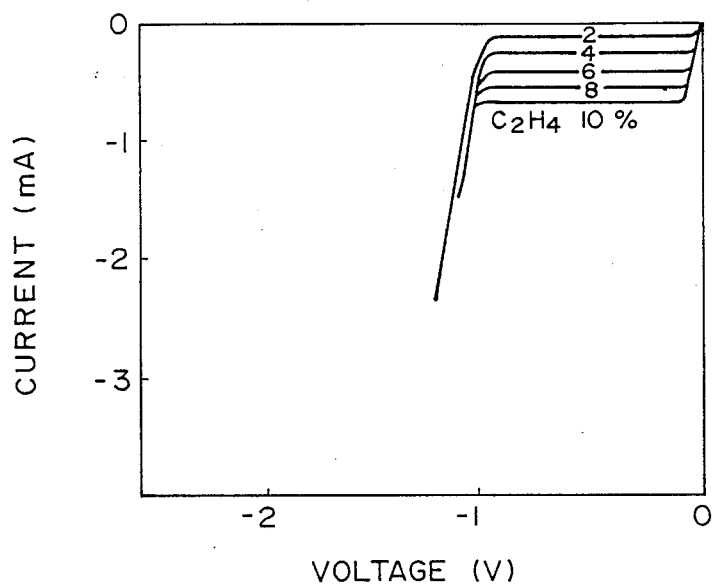
FIG. 9A is a graph showing the current-voltage characteristics of the gas decomposition type hydrogen sensor.
Figure 9B:
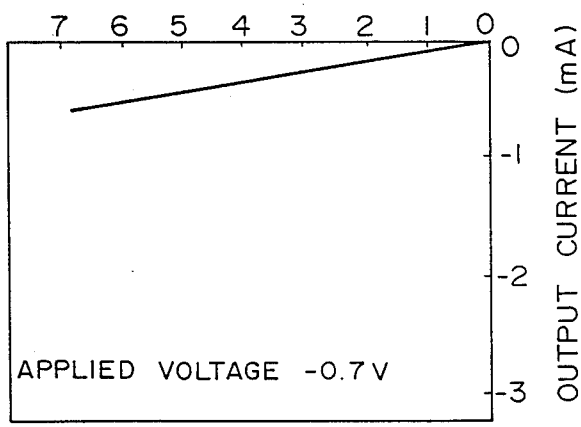
FIG. 9B is a graph showing the current-$C_2H_4$ concentration characteristics in the gas decomposition type hydrogen sensor.

FIGS. 7 to 9 show current-voltage characteristics resulting from tests performed when the concentration of $O_2$ is maintained constant while varying the concentration of the combustible gas and gas concentration-output current characteristics resulting from tests carried out when the applied voltage is maintained at a unvariable level equal to $-0.7$ V, these tests being performed for three gas systems, $H_2$—$O_2$—$N_2$, $CO$—$O_2$—$N_2$ and $C_2H_4$—$O_2$—$N_2$, respectively.

Figure 10:
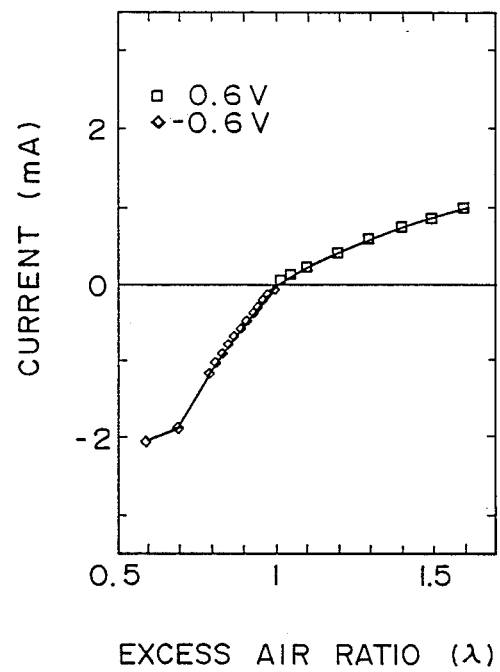
FIG. 10 is a graph showing the current-excess air ratio characteristics in the combination of the limiting current type oxygen detecting section with the gas decomposition type hydrogen detecting section.

FIG. 10 shows output current-excess air ratio characteristics in the combination of the limiting current type oxygen detecting section 2 with the gas decomposition type hydrogen detecting section 3, which are obtained from the fuel rich region to the fuel lean region. From this graph, it can be understood that the excess air ratio can substantially linearly be measured in both the fuel rich and lean regions. When these sensors are used for an air/fuel ratio detecting apparatus described hereinafter, therefore, outputs from the respective detecting sections can be added to one another under adjustment of gain such that the detection of air/fuel ratio will be performed with an improved accuracy over an increased measurement range.

Figure 11:
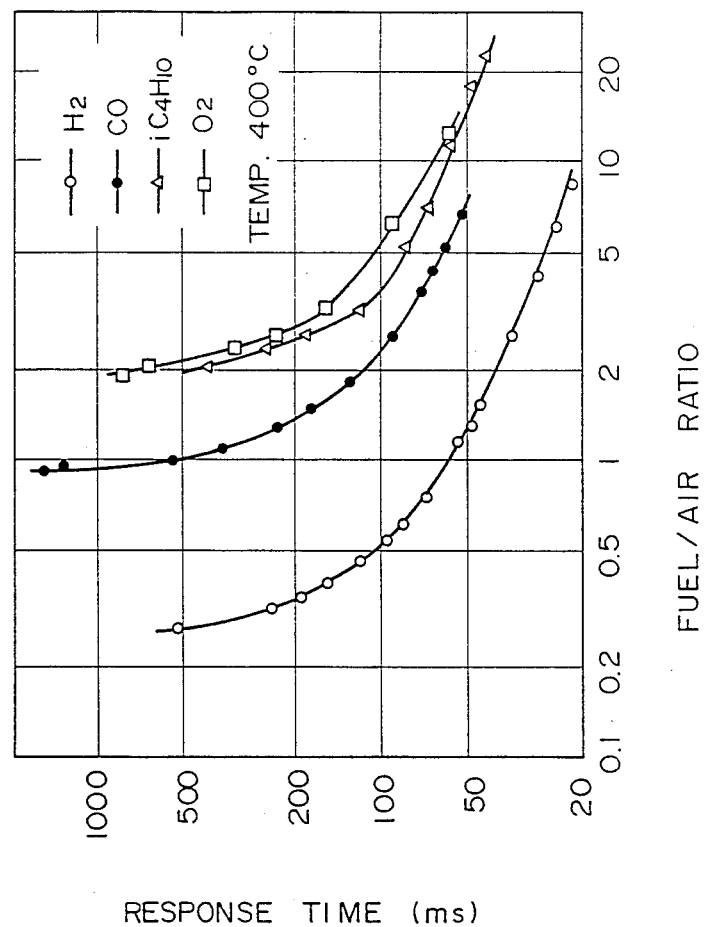
FIG. 11 is a graph illustrating the response characteristics of the air/fuel ratio sensor according to the present invention for various gases such as $H_2$, CO, $i-C_4H_{10}$ and $O_2$.

FIG. 11 shows responsibilities (50% responsibilities) of the wide-range air/fuel ratio sensor of the present invention with respect to various gases, that is, $H_2$, $CO$, $i$—$C_4H_{10}$ and $O_2$.

(II) Air/Fuel Ratio Detecting Apparatus

Figure 12:
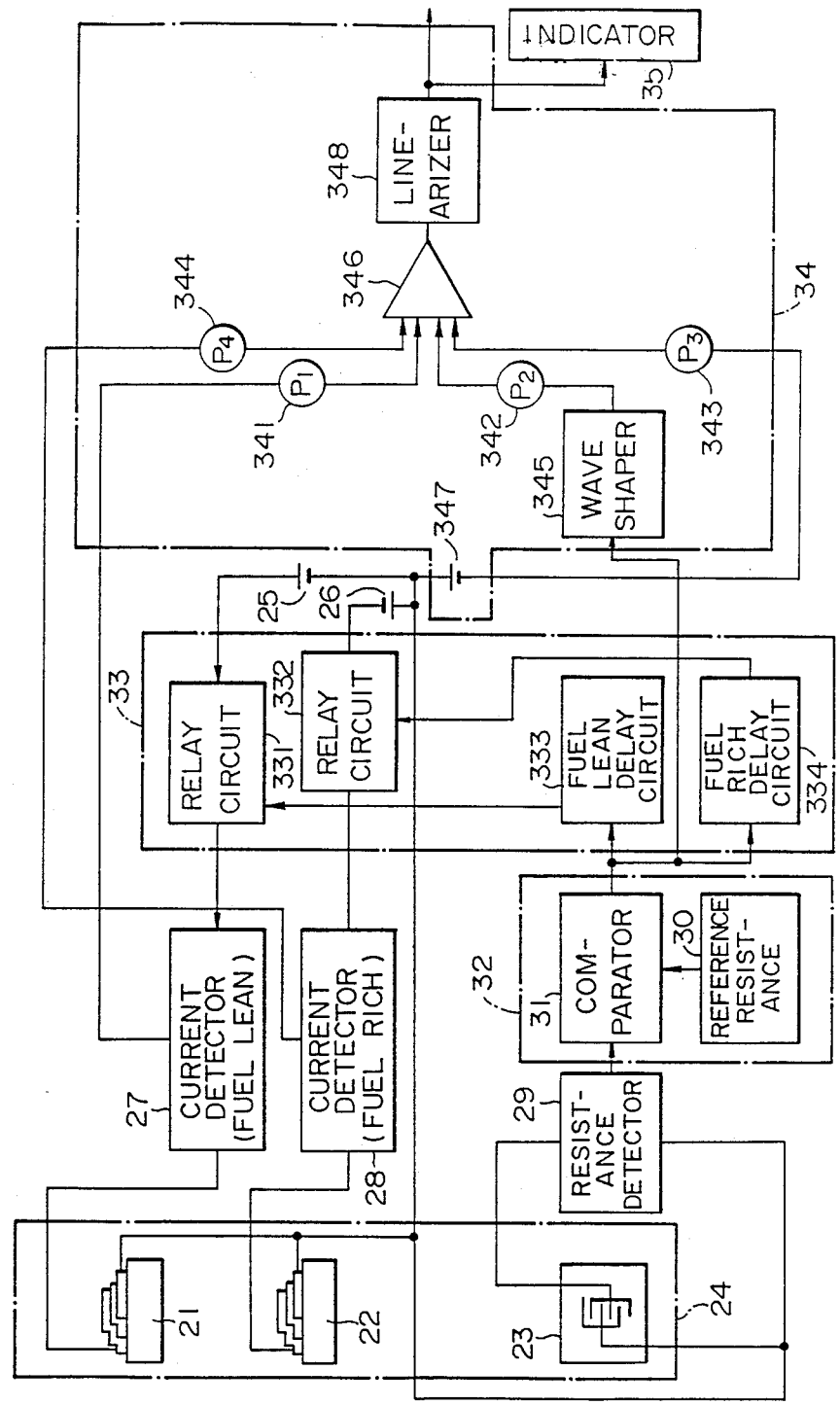
FIG. 12 is a block diagram of one embodiment of an air-fuel ratio detecting apparatus constructed in accordance with the present invention.

Referring now to FIG. 12, there is shown one embodiment of an air/fuel ratio detecting apparatus of the present invention, which comprises the air/fuel ratio sensor hereinbefore described in detail and a circuit for driving this air/fuel ratio sensor and processing the outputs thereof.

The air/fuel ratio detecting apparatus comprises a sensor section 24 including an integral unit which consists of a limiting current type oxygen detecting section 21, a gas decomposition type hydrogen detecting section 22 and a resistance-variable type oxygen detecting section 23, as described previously; a limiting current measuring voltage source 25 for applying a voltage to the limiting current type oxygen detecting section 21; a voltage source 26 for applying a voltage to the gas decomposition type hydrogen detecting section 22; a current detecting section 27 for measuring a current in the limiting current type oxygen detecting section 21; another current detecting section 28 for detecting a current in the gas decomposition type hydrogen detecting section 22; a resistance detecting section 29 for detecting a resistance in the resistance-variable type oxygen detecting section 23; a comparing/discriminating section 32 including a comparator 31 for comparing the output of the resistance detecting section 29 with the value of a reference resistance 30, whereby it can be discriminated whether the present state is in either of the fuel rich or lean region; a switching control section 33 for changing the limiting current type oxygen detecting section 21 to its operative position after a predetermined time period from a time when the comparing/discriminating section 32 discriminates the change from the fuel rich state to the fuel lean state and for changing the limiting current type oxygen detecting section 21 to its inoperative position when the comparing/discriminating section 32 discriminates the change from the fuel lean state to the fuel rich state; an output signal adding section 34 for adding output signals from the limiting current type oxygen detecting section 21, the resistance-variable type oxygen detecting section 23 and the gas decomposition type hydrogen detecting section 22 to generate a signal representative of the present air/fuel ratio from the added output signals; and an indicator 35 for indicating the output of the output signal adding section 34.

The switching control section 33 comprises a first relay circuit 331 for controlling the connection and disconnection between the limiting current measuring voltage source 25 and the limiting current type oxygen detecting section 21; a second relay circuit 332 for controlling the connection and disconnection between the gas decomposition type hydrogen detector voltage source 26 and the gas decomposition type hydrogen detecting section 22; a fuel lean delay circuit 333 for providing a predetermined delay time to the output of the comparing/discriminating section 32 to send it to the first relay circuit 331 as a fuel lean drive control signal; and a fuel rich delay circuit 334 for providing a predetermined delay time to the output of the comparing/discriminating section 32 to send it to the second relay circuit 332 as a fuel rich drive control signal.

The output signal adding section 34 includes an inversion adder 346 connected at its input with potentiometers 341, 342, 343 and 344 which serves as a level regulator. The inversion adder 346 is adapted to receive and add the output signals of the current detecting sections 27 and 28, the output signal of the comparing/discriminating section 32 and a D.C. bias signal of a negative D.C. bias source 347.

In this connection, the signal from the comparing/discriminating section 32 is inputted to the inversion adder 346 after waveform shaped at a waveform shaping circuit 345.

The features of the present invention will now be described with reference to their experimental results.

(a) Switching Between Both The Detecting Sections

Figure 13:
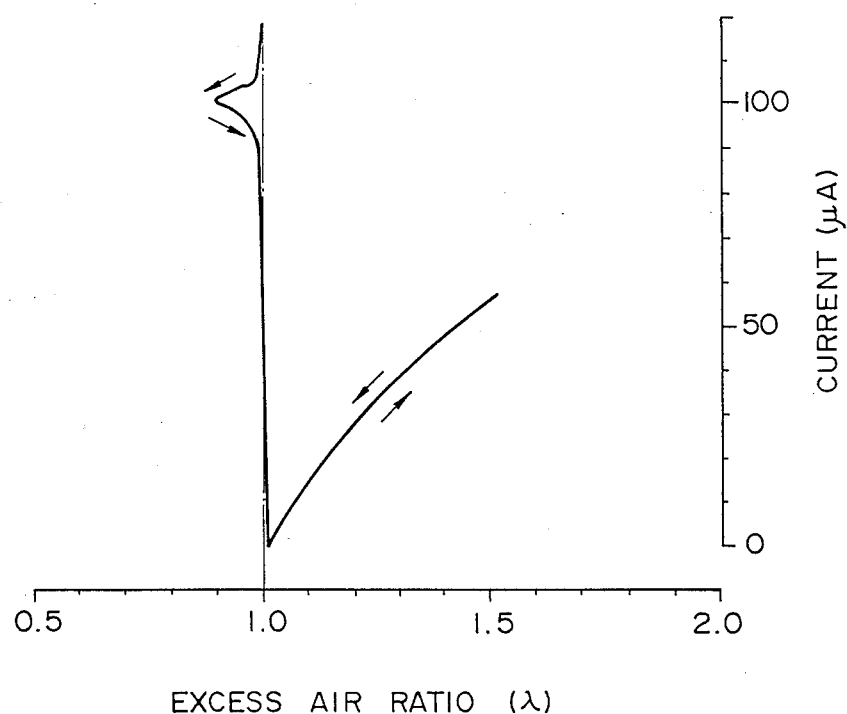
FIG. 13 is a graph showing the output current-excess air ratio characteristics of the limiting current type oxygen detecting section.

FIG. 13 shows the relationship between the current and the excess air ratio $\lambda$ at the limiting current type oxygen detecting section 21. From this graph, it will be apparent that a balanced relationship between the electric current and the excess air ratio $\lambda$ can be obtained in the fuel lean region in which the excess air ratio $\lambda$ is larger than one.

In the fuel rich region wherein the excess air ratio is smaller than one, however, the electric current increases independently of the value of the excess air ratio $\lambda$.

When it is wanted to determine the excess air ratio $\lambda$ from the measurements of electric current, two values of the excess air ratio must be considered relative to the same electric current level. This is called "two-valued function characteristics" which is extremely undesirable for the sensor.

At the gas decomposition type hydrogen detecting section 22, further, a balanced relationship between the excess air ratio and the detected current may be obtained in the fuel rich region wherein the excess air ratio $\lambda$ is smaller than one.

In accordance with the present invention, only one of both the detecting sections providing a more balanced relationship between the excess air ratio and the electric current can be selectively utilized. To this end, it is discriminated in the resistance-variable type oxygen detecting section 23 whether the ambient atmosphere is in either of the fuel rich or lean region. Based on such a discrimination, one of the voltage sources for driving the limiting current type oxygen detecting section 21 or the gas decomposition type hydrogen detecting section 22 is selected. In the present embodiment, such a selection is accomplished by means of the switching control section 33.

Figure 14:
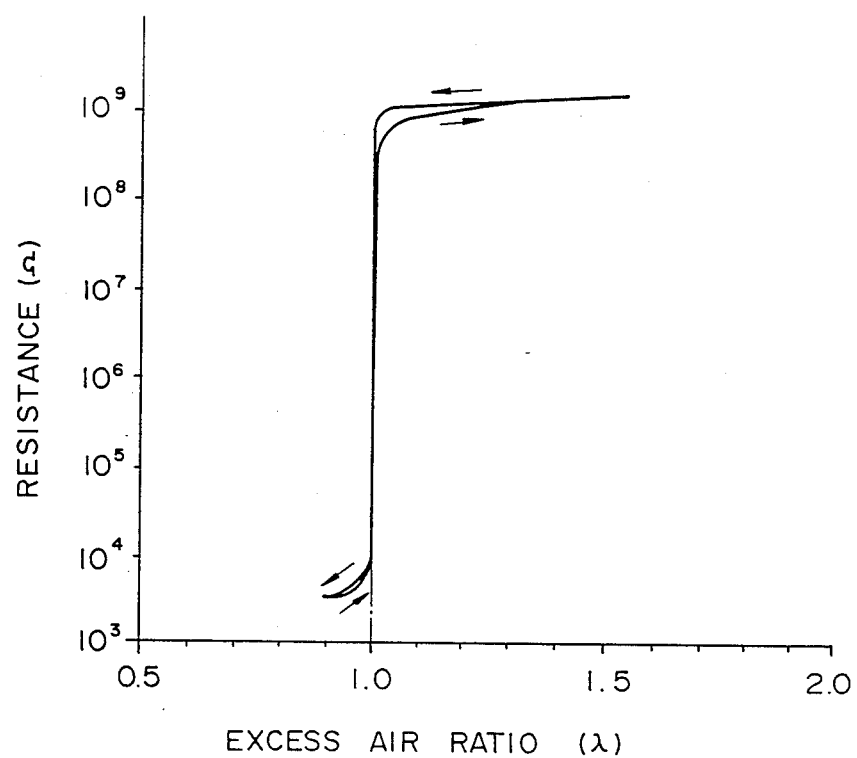
FIG. 14 is a graph showing the resistance-excess air ratio characteristics in the resistance-variable type oxygen detecting section.

FIG. 14 exemplifies characteristics of the resistance-variable type oxygen detecting section 23 of oxide semiconductor. From this figure, it will be apparent that the resistance of the oxygen detecting section 23 abruptly varies at the excess air ratio $\lambda = 1$. Thus, such resistance can be detected by the resistance detecting section 29 and then compared with the reference resistance 30 (for example, 106 Ohms) at the comparator 31 to determine whether the ambient atmosphere is in the fuel rich or lean region.

If in the fuel lean region, a voltage is applied to the limiting current type oxygen detecting section 21 so that the latter will be switched to its operative position. On the other hand, if it is discriminated that the ambient atmosphere is in the fuel rich region, a voltage is applied to the gas decomposition type hydrogen detecting section 22 to switch it to its operative position. As a result, the apparatus will be used without being related with the aforementioned "two-valued function". The above voltages are applied to the corresponding sections from the relay circuits 331 and 332, respectively.

It is required that the resistance-variable type oxygen detecting section 23 is rapidly operated. In such a case, each of the relay circuits should be delayed in energization by providing a delay time after the change from the fuel rich state to the fuel lean state (in the illustrated embodiment, 300 ms.). To this end, the fuel lean and rich delay circuits 333 and 334 are provided as shown in FIG. 12. Each of these delay circuits 333 or 334 functions to delay the corresponding relay circuit when the switching is carried out, such that the limiting current type oxygen detecting section 21 operates only on the fuel lean side or that the gas decomposition type hydrogen detecting section 22 operates only on the fuel rich side. On changing from the fuel rich region to the fuel lean region or vice versa, therefore, there will not be produced any spike noise. As a result, an extremely improved detection of air/fuel ratio can be attained in accordance with the present invention.

(b) Addition of Output Signals From Both The Detecting Sections

Figure 15:
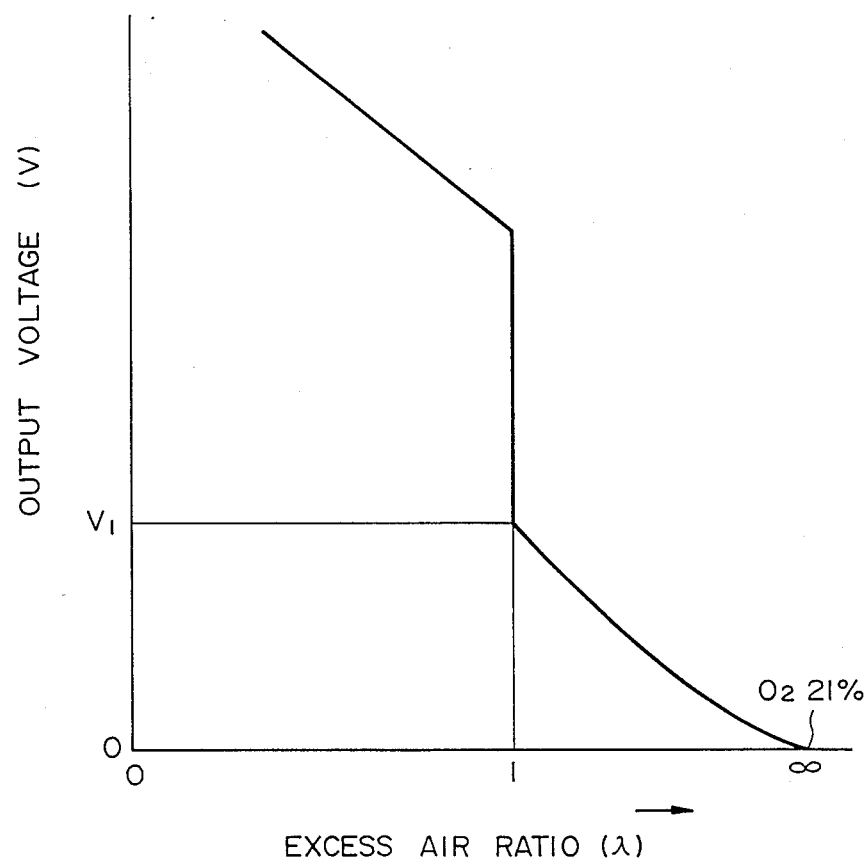
FIG. 15 is a graph showing composite output characteristics which is a target in the present invention.

FIG. 15 shows output characteristics at the inversion adder 346 of the output signal adding section 34, which is a target in the present invention. From this graph, it will be apparent that the output of the inversion adder 346 is larger than $V_1$ in the fuel rich region, abruptly decreases to $V_1$ at the excess air ratio $\lambda = 1$, continuously decreases in the fuel lean region and finally becomes zero at the excess air ratio $\lambda = \infty$. In order to provide such a one-dimensional output different as the above output characteristics wherein the output does not change between positive and negative values, the output signal adding section 34 is so arranged as shown in FIG. 12.

Figure 16:
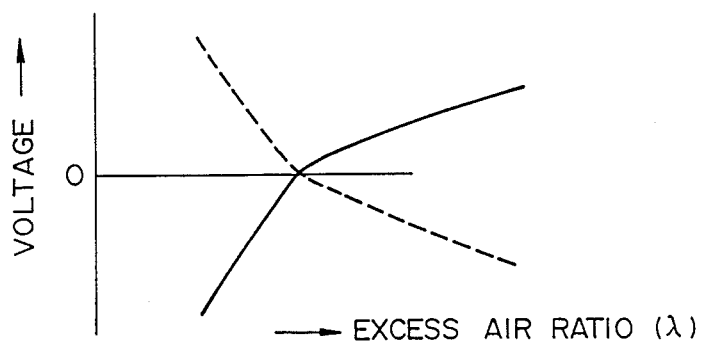
FIG. 16 is a graph showing the relationship between the composite signal consisting of the output signal from the limiting current type oxygen detecting section and the output signal from the gas decomposition type hydrogen detecting section and the excess air ratio.

When the outputs of the detecting sections 21 and 22 are converted into output voltages corresponding to the detected current levels at the current detecting sections 27 and 28 and multiplied by a proportional efficient at the potentiometers P1 and P4 to totalize the multiplied values, the voltage becomes a positive value proportional to the excess air ratio in the fuel lean region wherein $\lambda$ is larger than one and becomes a negative value proportional to the excess air ratio in the fuel rich region wherein $\lambda$ is smaller than one, as shown by solid line in FIG. 16. If only such a signal is passed through the inversion adder 346, the voltage will follow the curve as shown by broken line in FIG. 16. It is inconvenient that the output voltage changes between two positive and negative polarities depending on the value of $\lambda$. The output voltage is converted into an output having a single polarity by utilizing the output of the comparing/discriminating section 32 as will be described below.

Figure 17:
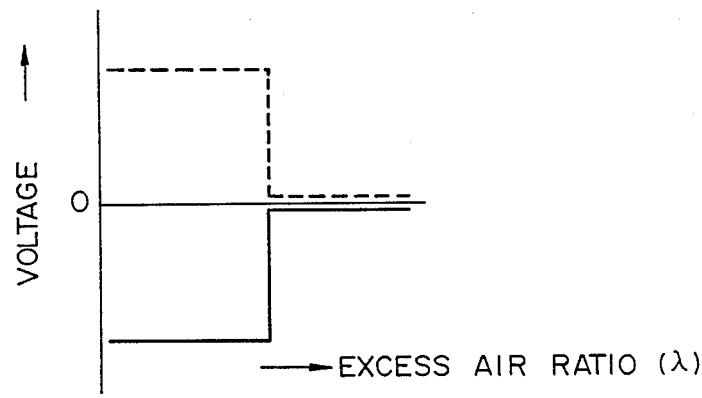
FIG. 17 is a graph showing the relationship between the output signal produced on the discrimination of the output from the resistance-variable type oxygen detecting section and the excess air ratio.

The output of the comparator 31 is shaped through the waveform shaping circuit 345 such that the output of the comparator will be a constant negative voltage for the fuel rich region and zero for the fuel lean region. When the resulting voltage is multiplied by a proportional coefficient at the potentiometer P2, there is obtained a curve as shown by solid line in FIG. 17. If only such a signal is passed through the inversion adder 346, there is obtained a curve as shown by broken line in FIG. 17.

Figure 18:
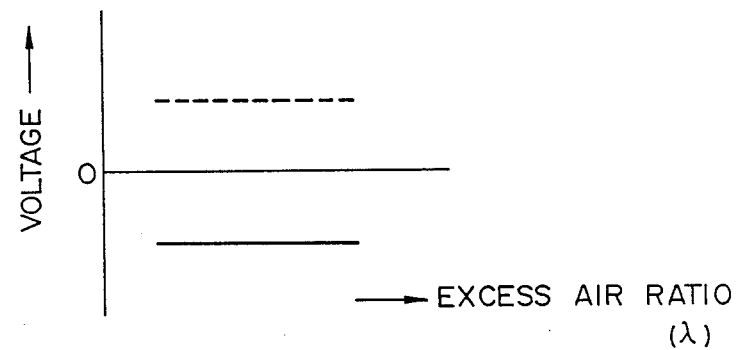
FIG. 18 is a graph showing the relationship between the bias voltage and the excess air ratio.

A constant negative voltage is then applied from the voltage source 347 to the potentiometer P3 to provide a signal shown by solid line in FIG. 18. If only such a signal is passed through the inversion adder 346, there can be obtained a signal shown by broken line in FIG. 18.

Since the three solid-line signals mentioned above are added and inversion-processed by the inversion adder 346, the totalized signal from the three broken-line signals is actually generated at the output of the inversion adder 346. This results in such an output as shown in FIG. 16.

(c) Linearization of Composite Signal

Figure 19:
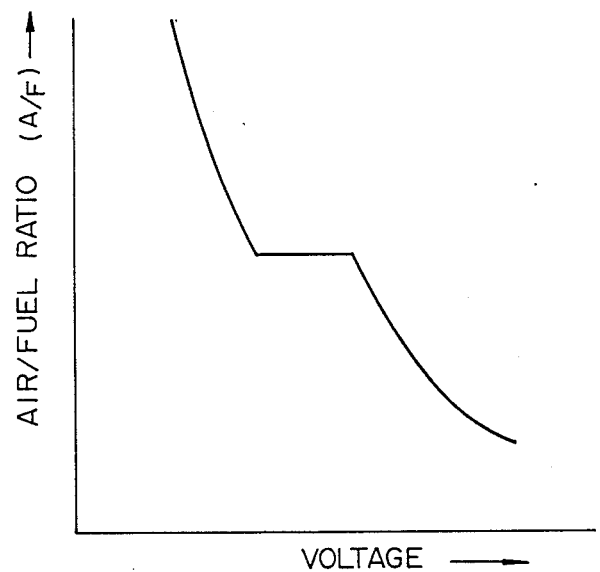
FIG. 19 is a graph showing the chaaracteristics of a linearizer.
Figure 20:
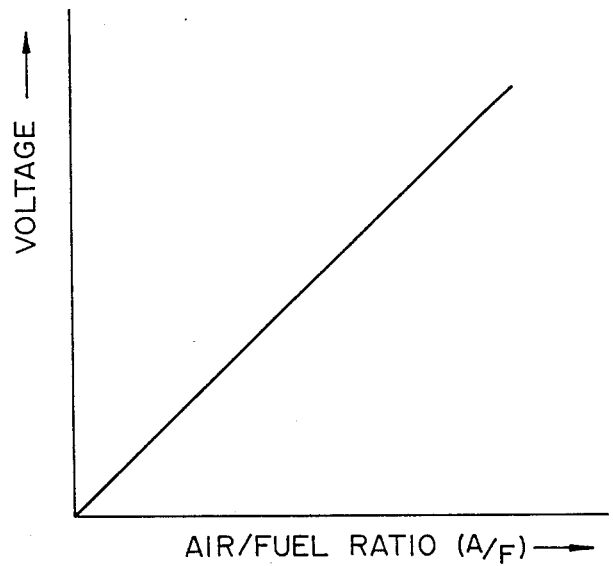
FIG. 20 is a graph showing the overall characteristics resulting from the linearization by the linearizer.

As shown in FIG. 10, the electric current from the sensor has a smaller gradient for the excess air ratio in the region wherein $\lambda$ is larger than one and a larger gradient in the region wherein $\lambda$ is smaller than one. And yet, both the regions do not provide any linear relation if defined precisely. This tends to generate errors on measurements of the excess air ratio. It is therefore preferred that a linearizer 348 is provided when it is desired to improve the accuracy of measurement. In the present embodiment, a linearizer 348 is connected with the inversion adder 346 on its downstream side. The linearizer 348 may have characteristics as shown in FIG. 19. FIG. 20 shows characteristics resulting from the linearization by the linearizer 348.

We claim:
1. A wide-range air/fuel ratio sensor comprising:
   a porous alumina substrate;
   a limiting current type oxygen detecting section for detecting the air/fuel ratio in the fuel lean region of a predetermined gas atmosphere, said limiting current type oxygen detecting section being of a laminated construction which consists of a first gas permeable electrode layer formed on said porous alumina substrate, a solid electrolytic layer on said first electrode layer and a second gas permeable electrode layer on said solid electrolytic layer;
   a resistance-variable type oxygen detecting section for detecting the excess air ratio $\lambda$ when $\lambda$ is equal to one, said resistance-variable type oxygen detecting section consisting of an oxide semiconductor layer on said porous alumina substrate and a pair of opposed electrodes on the same substrate;

13 a gas decomposition type hydrogen detecting section for detecting the air/fuel ratio in the fuel rich region, said hydrogen detecting section being of a laminated construction which consists of a second gas permeable electrode layer on said porous alumina substrate, a solid electrolytic layer on said second electrode layer and a first gas-permeable electrode layer on said solid electrolytic layer; and heater means for heating the respective detecting sections to their optimum temperature in operation.

2. A wide-range air/fuel ratio sensor as defined in claim 1 wherein said porous alumina substrate has a porosity ranged from 2% to 40% and a pore diameter ranged from 0.02 μm to 1.2 μm.

3. A wide-range air/fuel ratio sensor as defined in claim 1 wherein said limiting current type oxygen detecting section is of a laminated construction consisting of a first gas-permeable cathode electrode made of platinum and disposed on said porous alumina substrate, a solid electrolytic layer disposed on said first cathode electrode and made of $ZrO_2+Y_2O_3$ which has a crystalline orientation in a particular direction and a film thickness ranged from 0.1 μm to 30 μm and a second gas-permeable anode electrode made of platinum and disposed on said solid electrolytic layer.

4. A wide-range air/fuel ratio sensor as defined in claim 1 wherein said resistance-variable type oxygen detecting section comprises an oxide semiconductor layer on said porous alumina substrate and made of niobium pentaoxide ($Nb_2O_5$) and a pair of opposed electrodes formed on the same substrate.

5. A wide-range air/fuel ratio sensor as defined in claim 1 wherein said gas decomposition type hydrogen detecting section is of a laminated construction consisting of a second gas-permeable anode electrode disposed on said porous alumina substrate and made of platinum, a solid electrolytic layer disposed on said second anode electrode and made of $ZrO_2+Y_2O_3$ which has a crystalline orientation in a particular direction and a film thickness ranged from 0.1 μm to 30 μm, and a first gas-permeable cathode electrode disposed on said solid electrolytic layer and made of platinum.

6. A wide-range air/fuel ratio sensor as defined in claim 1 wherein said heater means comprises a plurality of heaters made of platinum and wherein each of said heaters is formed on the underside of said porous alumina substrate at a position corresponding to the respective detecting section to be heated by said heater.

7. A wide-range air/fuel ratio detecting apparatus comprising:
  a porous alumina substrate;
  a limiting current type oxygen detecting section mounted on said porous alumina substrate for detecting the air/fuel ratio in the fuel lean region of a predetermined gas atmosphere;
  a resistance-variable type oxygen detecting section mounted on said porous alumina substrate for detecting the excess air ratio λ when λ is equal to one;
  a gas decomposition type hydrogen detecting section mounted on said porous alumina substrate for detecting the air/fuel ratio in the fuel rich region;
  a comparing/discriminating section for comparing the output of said resistance-variable type oxygen detecting section with a reference value and discriminating whether the ambient atmosphere is in either of the fuel rich or lean region;
  wherein said apparatus drives either one of said limiting current type oxygen detecting section or gas decomposition type hydrogen detecting section depending on the discriminated result from said comparing/discriminating section.

8. A wide-range air/fuel ratio detecting apparatus as defined in claim 7 wherein said apparatus further comprises heater means for heating said limiting current type oxygen detecting section, said resistance-variable type oxygen detecting section and said gas decomposition type hydrogen detecting section to their optimum temperatures in operation.

9. A wide-range air/fuel ratio detecting apparatus as defined in claim 8 wherein:
  said limiting current type oxygen detecting section is of a laminated construction which consists of a first gas-permeable electrode layer formed on said porous alumina substrate, a solid electrolytic layer on said first electrode layer and a second gas-permeable electrode layer on said solid electrolytic layer;
  said resistance-variable type oxygen detecting section consists of an oxide semiconductor layer on said porous alumina substrate and a pair of opposed electrodes on the same substrate;
  said gas decomposition type hydrogen detecting section is of a laminated construction which consists of a second gas-permeable layer on said porous alumina substrate, a solid electrolytic layer on said second electrode layer and a first gas-permeable electrode layer on said solid electrolytic layer; and
  said apparatus further comprising:
  a switching control section in respose to said comparing/discriminating section for changing said limiting current type oxygen detecting section to its operative position and also said gas decomposition type hydrogen detecting section to its inoperative position when said comparing/discriminating section discriminates the change from the fuel rich state to the fuel lean state and for changing said limiting current type oxygen detecting section to its inoperative state and also said gas decomposition type hydrogen detecting section to its operative position when said comparing/discriminating section discriminates the change from the fuel lean state to the fuel rich state; and
  an output signal adding section for adding the output signals from said limiting current type oxygen detecting section and gas decomposition type hydrogen detecting section to generate a signal representative of an air/fuel ratio.

10. A wide-range air/fuel ratio detecting apparatus as defined in claim 9 wherein said comparing/discriminating section is of a comparator for comparing the resistance value in said resistance-variable type oxygen detecting section with that of a reference resistance.

11. A wide-range air/fuel ratio detecting apparatus as defined in claim 9 wherein the reference value in said comparing/discriminating section is set at a relatively high level such that the discrimination of the change from the fuel lean state to the fuel rich state can be promoted.

12. A wide-range air/fuel ratio detecting apparatus as defined in claim 9 wherein said switching control section comprises a first relay circuit for controlling a drive current to be supplied to said limiting current type oxygen detecting section, depending on the output of said comparing/discriminating section; a second relay circuit for controlling a drive current to be supplied to said gas decomposition type hydrogen detecting section, depending on the output of said comparing/discriminating section; a fuel lean delay circuit connected between said comparing/discriminating section and said first delay circuit and adapted to provide a delay time for the output of said comparing/discriminating section to be send to said first delay circuit; and a fuel rich delay circuit connected between said comparing/discriminating section and said second relay circuit and adapted to provide a delay time for the output of said comparing/discriminating section to be fed to said second relay circuit.

13. A wide-range air/fuel ratio detecting apparatus as defined in claim 9 wherein said resistance-variable type oxygen detecting section comprises an oxide semiconductor layer on said porous alumina substrate and made of niobium pentaoxide ($Nb_2O_5$) and a pair of opposed electrodes formed on the same substrate.

14. A wide-range air/fuel ratio detecting apparatus as defined in claim 13, further comprising a linearizer connected with said inversion adder on its downstream side, said linearizer being adapted to perform the linearization of the output signal from said inversion adder.

* * * * *